United States Patent [19]

Wade et al.

[11] Patent Number: 5,710,193

[45] Date of Patent: Jan. 20, 1998

[54] PHOTOPOLYMERISABLE COMPONENTS OF RADIATION SENSITIVE COMPOSITIONS

[75] Inventors: John Robert Wade, Leeds; Michael John Pratt, Ilkley; Jianrong Ren, Leeds, all of United Kingdom

[73] Assignee: DuPont (UK) Limited, Stevenage, United Kingdom

[21] Appl. No.: 646,808

[22] Filed: May 21, 1996

Related U.S. Application Data

[63] Continuation of Ser. No. 6,549, Jan. 21, 1993, abandoned.

[30] Foreign Application Priority Data

Jan. 21, 1992 [GB] United Kingdom ............... 9201269

[51] Int. Cl.$^6$ ............... C08F 2/50; C08G 18/10; C08G 18/71; C08G 18/40
[52] U.S. Cl. ............... 522/35; 522/69; 522/904; 522/905; 522/90; 522/97; 522/174; 528/65; 528/66; 528/45; 528/68; 528/69; 430/270.1; 430/286.1
[58] Field of Search ............... 522/90, 97, 174, 522/35, 69, 904, 905; 528/45, 65, 66, 68, 69; 430/270.1, 286.1

[56] References Cited

U.S. PATENT DOCUMENTS

| | | | |
|---|---|---|---|
| 2,718,516 | 9/1955 | Bortnick | 260/86.1 |
| 2,821,544 | 1/1958 | Holtschmidt et al. | 260/486 |
| 2,882,259 | 4/1959 | Graham | 260/45.5 |
| 3,299,007 | 1/1967 | Suling et al. | 260/77.5 |
| 3,759,809 | 9/1973 | Carlick et al. | 204/159.23 |
| 3,825,479 | 7/1974 | Carlick et al. | 204/159.23 |
| 4,212,803 | 7/1980 | Kruckenberg | 260/154 |
| 4,218,372 | 8/1980 | Koerte | 260/196 |
| 4,316,949 | 2/1982 | Petrellis et al. | 430/159 |
| 4,358,476 | 11/1982 | Zimmer et al. | 522/97 |
| 4,722,947 | 2/1988 | Thanawalla | 522/120 |
| 4,999,271 | 3/1991 | Etherington et al. | 522/174 |

FOREIGN PATENT DOCUMENTS

| | | |
|---|---|---|
| 0 305 115 | 8/1988 | European Pat. Off. |
| 2 038 849 | 11/1979 | United Kingdom |
| 2 107 334 | 10/1982 | United Kingdom |
| WO 87/07278 | 12/1987 | WIPO |

OTHER PUBLICATIONS

Focal Press London, New York, "Anti–Halation Backing" and Halation, The Focal Encyclopedia of Photography Revised Desk Edition, 1969, ISBN 0-240-50680-4, 50 and 727, 1969.

W&R Chambers Limited & Cambridge University Press—Edinburgh, Cambridge, 1988, Definitions of "Antihalation" and Halation, Chambers Science and Technology Dictionary P.M.B. Walker (Ed), ISBN 0-550-13239-2, 41 and 411, 1988.

W&R Chambers Limited—Edinburgh, New York 1990, Definitions of "Antihalation" and Halation , Chambers English Dictionary, S.I. Landau, W.S. Ramson (Consultant Eds.), ISBN 0-550-10250-7, 57 and 640, 1990.

Focal Press London, New York, 1973, "Anti–Halation Backing", Graphic Reproduction Photography—J.W. Burden, ISBN 0-240-50757-6, 151 and 152, 1973.

JP 48057620, Abstract, Hitachi Chemical Co. Ltd. (HITA), Kind A, JP7192411 (1971, Nov. 19).

Chemical Abstracts, vol. 80, p. 74, No. 38395, J 73-08,562 Mar. 15, 1973.

Abstracts 86-045874/07, J6 1000272-A Dec. 6, 1984.
Abstract 89-238899/33, J0 1174-575-A Dec. 19, 1987.
Abstract 88-281581/40; J6 3205-650-A Feb. 20, 1987.
Abstract JP86-70883 Mar. 31, 1986.

Primary Examiner—Susan W. Berman

[57] ABSTRACT

Colorants, polymeric binder resins, photoinitiators, photosensitizers, color-change agents, anti-halation agents, stabilizers, and other active hydrogen-containing components of radiation sensitive compositions for lithographic printing plate production and the like are reacted with a polyethylenically unsaturated monoisocyanate compound of the formula

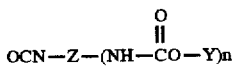

wherein Y is the residue of a monohydroxyl compound of formula YOH and Y contains at least two ethylenically unsaturated double bonds. In this way the components are bonded to the image on exposure.

8 Claims, No Drawings

PHOTOPOLYMERISABLE COMPONENTS OF RADIATION SENSITIVE COMPOSITIONS

This is a continuation of application Ser. No. 08/006,549, filed Jan. 21, 1993, now abandoned.

This invention relates to photopolymerisable components of radiation sensitive compositions and is concerned with such components which include a plurality of polymerisable ethylenic double bonds.

Radiation sensitive plates for use in the production of lithographic printing plates comprise a substrate, e.g. of suitably treated, aluminium, coated with a radiation sensitive composition. In use, the composition is image-wise exposed to actinic radiation which changes the solubility of the areas struck by the radiation. Thereafter, the more soluble areas are selectively removed by means of a developer liquid to leave an image constituted by the less soluble areas.

Photopolymerisable compositions have widely been employed as the radiation sensitive compositions in negative-working lithographic plates. Generally, such printing plates have high durability enabling long printing runs to be completed. Also such printing plates often have high sensitivity allowing very short exposure times to be employed. A photopolymerisable composition for use in negative lithographic plates typically comprises a photopolymerisable ethylenically unsaturated monomer, a photoinitiator or sensitizer and other non-polymerisable components such as a polymeric binder resin, a colorant such as a dye and, optionally, a diazonium compound to prevent oxygen inhibition of photopolymerisation. In the compositions without a diazonium compound, an oxygen barrier layer is often required. There are, however disadvantages associated with such compositions notably: a) colour loss on development due to leaching of the dye, used as colorant, by the developer liquid; b) inadequate wear resistance resulting from the fact that the polymeric binder (which provides the wear resistance) is not photopolymerisable; c) loss of photopolymerisation efficiency on storage associated with migration of the photoinitiator or sensitizer out of the radiation sensitive composition; and d) incompatibility of the photopolymerisable monomer and the other components caused by the difference in their physical forms which leads to instability and hence poor shelf-life of the composition.

It has been found that these disadvantages can be overcome by chemically combining the non-polymerisable components of the composition with a compound having the important features of i) containing a plurality of photopolymerisable ethylenic double bonds enabling efficient photopolymerisation to be effected on exposure to actinic radiation; and ii) being substantially free of impurities ensuring the stability of the compositions. The components are thereby chemically bonded to the image matrix after exposure, thus providing improved properties such as enhanced colour contrast after development and increased wear resistance. Preferably the compound also possesses a similar physical form to that of the polymerisable monomer in the composition to improve the homogeneity of the physical form of the composition. The molecular weight of the compounds should preferably be sufficiently high to prevent migration of components such as the photoinitiator or sensitizer.

It has already been proposed to combine components of radiation sensitive compositions with compounds containing ethylenic double bonds. More particularly, reaction products of such components with a compound containing a single acrylate group have been described, but such products are inadequate for use in radiation sensitive compositions due to their low acrylate content which leads to inefficiency in the photopolymerisation process. Their main use has been in solution free-radical polymerization reactions for polymers. Reaction products of components of radiation sensitive compositions with compounds containing a plurality of ethylenic double bonds have been disclosed in the context of the manufacture of printing inks and decorative coatings. Such products are, however, exclusively mixtures of the desired product with a substantial amount of associated impurities which are unsuitable for lithographic printing plate applications due to stability problems.

UK patent specification 2,038,849 discloses a 'structurally coloured compound' derived from the reaction between a reactive hydrogen atom-containing dye, a polyisocyanate and a hydroxyl compound containing a plurality of ethylenically unsaturated double bonds. An 'in-situ' method of synthesis is described whereby the dye is first reacted with a polyisocyanate such as tolylene-2,4-diisocyanate and, without isolating the intermediatory product, an ethylenically unsaturated hydroxyl compound is added to the reaction mixture. The final product obtained is a mixture, typically containing up to 15% by-products.

European patent specification No. 136452 and U.S. Pat. No. 4,722,947 both disclose polymeric materials containing polymerisable ethylenic double bonds. These polymers are characterized by a single ethylenic double bond attached to one reactive site (such as an OH group) and therefore the total content of such double bonds in relation to the polymer is low. It is known that polymers of this type have low efficiency of photopolymerisation.

Japanese patent application 8939698 discloses a novolak epoxy resin modified with a compound containing a number of ethylenic double bonds, pentaerythritol triacrylate and a diisocyanate using an 'in-situ' method. A consequence of such a method is a large increase in the molecular weight of the product or, in some cases, gelation.

There are numerous disclosures of isocyanate compounds containing a single acrylate group. For example, U.S. Pat. Nos. 2,718,516, 2,821,544, 2,882,259, 3,299,007, and 3,453,223, disclose various methods for synthesizing isocyanato ethyl methacrylate and DE-OS-3,523,692 discloses a method for synthesizing 4-isocyanato butyl methacrylate. These ethylenically unsaturated isocyanates can be used to introduce ethylenic double bonds into components of radiation sensitive compositions. However, the efficiency of polymerization of the thus modified components is inadequate for use.

Prior to the present invention, isocyanato compounds containing a plurality of ethylenic double bonds had not been isolated as a pure product. Japanese Patent Application number 1174515 describes a number of such compounds for use in floor coatings. The compounds are, however, mixtures containing a significant proportion of starting materials, such as diisocyanate, with high toxicity and are unsuitable for use in radiation sensitive compositions.

It is an object of the present invention to provide photopolymerisable compounds useful in radiation sensitive compositions which carry a plurality of photopolymerisable groups containing ethylenically unsaturated double bonds and which are very effective in radiation sensitive compositions. Preferred compounds include those derived from colorants, polymeric binder resins, photoinitiators, photosensitizers, colour-change agents, anti-halation agents, stabilizers, and other components of radiation sensitive compositions for lithographic printing plate production and the like.

It is another object of the present invention to provide an efficient method for producing such photopolymerisable compounds with no undesired side-reactions and with the minimum amount of associated impurities. This object can be achieved by providing a pure intermediate compound which includes, in a single molecule, a single isocyanate group and a plurality of photopolymerisable ethylenically unsaturated groups. By virtue of the isocyanate group, the compound can be reacted with any component containing a reactive hydrogen group, such as a hydroxy, mercapto or amino group, whereby the photopolymerisable groups are introduced into the component and thereby such components are bonded to the image on exposure as a result of polymerization of the photopolymerisable groups.

It is yet another object of the present invention to provide components of radiation sensitive compositions with an improved physical form in order to reduce the problems of incompatibility and migration of the components.

According to one aspect of the present invention, there is provided a polyunsaturated compound having the general formula 1:

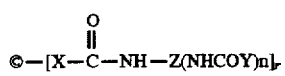
$$\quad 1$$

where ⓒ represents the residue of an active hydrogen containing compound of the formula ⓒ-(XH)r where XH is a hydroxyl group, a mercapto group or a primary or secondary amino group; r is an integer ranging from 1 to 10 for a simple molecule and from 1 to 10,000 for a polymeric macromolecule; Z represents the residue of a polyisocyanate OCN—Z—(NCO)n where n is 1 or 2; and Y is the residue of a monohydroxyl compound of the formula YOH where Y contains at least two ethylenically unsaturated double bonds.

The compound of the formula ⓒ-(XH)r is preferably a component of a radiation sensitive composition such as (i) an organic colorant or chromophore functioning as a shading dye or colour-change dye such as described by formulae 2–7, or an anti-halation reagent such as described by formulae 8–11, or a sensitizer such as described by formulae 12–16;

(ii) a photo active material such as an organic azide as described by formulae 17–20 or a photoinitiator as described by the Ketone derivatives of formulae 21–26;

(iii) a polymeric binder resin such as a poly(vinyl acetal), a styrene-allyl alcohol copolymer, an acrylic co- or terpolymer containing hydroxy alkyl methacrylate, a novolak resin or a poly(vinyl phenol); and (iv) an isocyanate blocking agent such as an oxime, a phenol or a caprolactam.

According to another aspect of the present invention, there is provided a process for producing a polyunsaturated compound of formula 1 which comprises reacting a compound of the formula ⓒ-(XH)r with an ethylenically unsaturated mono isocyanate compound of the formula:

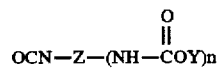
$$\quad 27$$

to obtain the desired compound.

The polyethylenically unsaturated mono isocyanate compound of formula 27 is the reaction product of a polyisocyanate of the formula

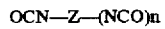     28 where n may be 1 or 2, and an ethylenically unsaturated monohydroxy compound of the formula YOH carrying at least two ethylenically unsaturated double bonds.

In formula 27, Z may be, for example, an aromatic, alicyclic, or heterocyclic ring. It may also be an alkylene group. Examples of such polyisocyanates are shown by formulae 42 to 52.

The ethylenicaliy unsaturated monohydroxy compound of the formula YOH may be of the following detailed general formula:

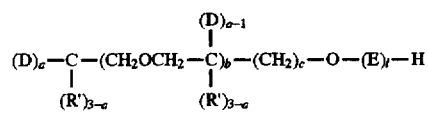
$$\quad 29$$

where:

a=2 or 3 b=0 or 1 c=0 or 1

R'=H or alkyl l=0 or 1

In formula 29, D has the structure:

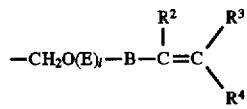
$$\quad 30$$

where

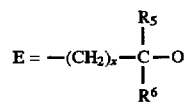

B=single bond, —CH₂—, or

x=1 to 3

R²=H or CH₃

R³=H or CH₃

R⁴=H or CH₃

R⁵=H or CH₃

R⁶=H or CH₃

Examples of suitable poly ethylenically unsaturated monohydroxy compounds are glycerol diacrylate, trimethylolpropane diacrylate, pentaerythritol triacrylate, ditrimethylolpropane triacrylate, tetra(hydroxypropyl)pentaerythritol triacrylate, dipentaerythritol pentaacrylate and pentaerythritol triallyl ether.

The ethylenically unsaturated monohydroxy compound of formula 29 is preferably prepared from a saturated polyol by reacting all except one of the hydroxy groups with an ethylenically unsaturated compound including a functional group capable of reacting with a hydroxy group. Such polyols are abundant and suitable examples are glycerol, trimethylolethane, trimethylolpropane, pentaerythritol, dipentaerythritol or polyhydroxyl compounds resulting from the oxyalkylation of polyols with alkylene oxide, in particular ethylene oxide or propylene oxide.

In accordance with a particular embodiment of the invention, the reaction between the polyisocyanate of formula 28 and the polyunsaturated mono hydroxy compound of formula YOH is effected in such a way that the ethylenically unsaturated mono isocyanate compound of formula 27 is produced in a manner such as to avoid the formation of the large amount of by-products which are ordinarily produced when polyisocyanates are reacted with reactive hydrogen-containing compounds. In accordance with this embodiment, the reaction is carried out in a medium in which the reactants are miscible but in which the ethylenically unsaturated mono isocyanate compound is immiscible.

This can be achieved by, for example admixing the hydroxy compound of formula YOH with a solvent with which it is immiscible but with which it becomes miscible when the polyisocyanate is added. Then, as the reaction proceeds and the polyisocyanate concentration decreases, the ethylenically unsaturated mono isocyanate separates out first, thereby preventing further reaction of the remaining isooyanate group. The selective formation of the ethylenically unsaturated mono isocyanate of the invention can be assisted by using, as the polyisocyanate, an isocyanate having isocyanate groups of differing reactivities such as tolylene diisocyanate or isophorone diisocyanate.

Examples of preferred polyunsaturated monoisocyanates are shown by formulae 31 to 34.

The polyunsaturated mono isocyanate is reacted with a compound of the formula ⊙-(XH)r in an inert solvent, preferably, with the addition of a suitable catalyst such as dibutyltin dilaurate to afford the polyunsaturated lithographic plate component of the present invention. Suitable inert solvents are, for example, diethyl ether, tetrahydrofuran, methyl ethyl ketone, dimethylformamide, dimethyl sulphoxide, N-methyl pyrrolidinone or acetonitrile. Preferred examples of the resultant polyunsaturated lithographic plate components are shown by formulae 35 to 41.

The following Examples illustrate the invention.

EXAMPLE 1

Synthesis of Compound 31 (a polyacrylate mono isocyanate compound derived from tetra (hydroxypropyl)pentaerythritol triacrylate (THPT) and tolylene-2,4-diisocyanate (TDI))

In a 500 ml three-neck flask equipped with a mechanical stirrer and drying tube, 50 g of tetra(hydroxypropyl) pentaerythritol triacrylate (OH value 113) were stirred in 200 mls of petroleum ether (b.p. 40°–60° C.). Tolylene-2,4-diisocyanate (18.5 g, 0.12 mole, 20% excess) was added dropwise over 10 minutes. On completion of the addition, it was noticeable that THPT was not miscible with the mixture. A minimum amount of diethyl ether was added until a clear solution was obtained. Hydroquinone (0.05 g) and a catalytic amount of dibutyltin dilaurate were added and the reaction mixture was stirred at room temperature for 2 hours and then left standing for 16 hours. A viscous layer, no longer miscible with the solvent mixture, settled out. The top layer of solvents was decanted and the viscous residue washed with petroleum ether three times.

A liquid chromatographic method was used to determine the residual tolylene diisocyanate, and the total isocyanate content of the product was analyzed by titration. A total isocyanate content of 6.3% w/w was found against a theoretical value of 6.4% w/w. Therefore, the purity of the product was 98%.

EXAMPLE 2

Synthesis of Compound 32 (a polyacrylate mono isocyanate compound derived from THPT and isophorone diisocyanate (IPDI))

50 g of THPT (OH value 113) were reacted with isophorone diisocyanate (22.42 g, 0.1 mole) in a mixture of petroleum ether (b.p. 40°–60° C.) and diethyl ether according to the method of Example 1. A total isocyanate value of 5.6% w/w was found against a theoretical value of 5.8% w.w. Therefore, the purity of the product was 96.5%.

EXAMPLE 3

Synthesis of Compound 33 (a polyallyl ether mono isocyanate compound derived from pentaerythritol triallyl ether and TDI)

50 g of pentaerythritol triallyl ether (OH value 220) were reacted with 34 g of TDI (0.196 mole) in petroleum ether (b.p. 40°–60° C.) according to the method of Example 1. A total isocyanate content of 9.0% w/w was found against a theoretical value of 9.3% w.w. Therefore, the purity of the product was 96.7%.

EXAMPLE 4

Synthesis of Compound 34 (a polyacrylate mono isocyanate derived from dipentaerythritol pentaacrylate (DPEPA) and TDI)

50 g of dipentaerythritol pentaacrylate (OH value 110) was reacted with TDI (20 g, 0.12 mole, 20% excess) in a mixture of petroleum ether (b.p. 40°–60° C.) and diethyl ether according to the method of Example 1. A total isocyanate value of 5.8% w/w was found against a theoretical value of 6.1% w.w. Therefore, the purity of the product was 95%.

EXAMPLE 5

Synthesis of a photocrosslinkable epoxy Bisphenol A polymer (Epikote 1004)—(Compound 35)

A commercial epoxy Bisphenol A polymer marketed as Epikote 1004 by Shell with an average hydroxy value of 148 (10.0 g) was dissolved in 100 mls of dry methyl ethyl ketone, with the addition of 0.05 g of hydroquinone and a catalytic amount of dibutylin dilaurate. Compound 31 (7.4 g) was dissolved in 20 mls of methyl ethyl ketone and added to the polymer solution dropwise over a period of 10 minutes. On completion of the addition, the reaction mixture was heated to reflux until all residual isocyanate groups had disappeared. The solution was sprayed into 1 liter of water and a white powdery resin isolated. It was further washed with water in a blender twice and dried. $^1$H NMR indicated a total of 50% of the hydroxy groups had been modified as intended.

EXAMPLE 6 (Comparison)

Synthesis of a photocrosslinkable polymer using a prior art method (JP8939698)

The epoxy Bisphenol A polymer, Epikote 1004 (10.0 g) was dissolved in dry methyl ethyl ketone (100 mls) with the addition of a catalytic amount of dibutylin dilaurate. Tolylene diisocyanate (4.6 g) was added and the reaction mixture stirred at 40° C. in order to react 50% of the isocyanate groups. After 10 minutes, it was observed that gelation occurred, indicating premature crosslinking. The reaction was abandoned.

EXAMPLE 7

Synthesis of a photocrosslinkable copolymer of vinyl phenol and hydroxyethyl methacrylate (Lyncur CHM)—(Compound 36)

A commercial vinyl phenol and hydroxyethyl methacrylate copolymer marketed as LYNCUR CHM by Maruzen with an average hydroxy value of 120 (10.0 g) was modified using compound 31 according to the method of Example 5. ¹H NMR indicated a total of 50% of the hydroxy groups had been modified as intended.

EXAMPLE 8

Synthesis of a photocrosslinkable shading dye—(Compound 37)

A commercial liquid blue dye marketed by Milliken as Reactint Blue X3 with a hydroxy value of 205 and an average molecular weight of 550 (5.0 g) was dissolved in 100 mls of dry methyl ethyl ketone, with the addition of 0.05 g of hydroquinone and a catalytic amount of dibutylin dilaurate. 10.0 g of an isocyanate polyacrylate (compound 32) was dissolved in 20 mls of dry methyl ethyl ketone and added to the dye solution dropwise over 10 minutes. On completion of the addition, the reaction temperature was raised to reflux. The completion of the reaction was indicated by IR showing all isocyanate groups had disappeared. The solvent was then removed in vacuo to obtain the photocrosslinkable dye as a viscous liquid. The chemical structure of the product was determined by ¹H NMR and infrared spectroscopy.

EXAMPLE 9 (Comparison)

Synthesis of the photocrosslinkable dye of Example 8 using a prior art method

An attempt was made to form a photocrosslinkable dye from the commercial liquid blue dye, Reactint Blue X3 using the method of GB 2,038,849.

The hydroxy containing liquid dye (5.0 g) was dissolved in 50 mls of dry N,N-dimethyl formamide. 4.0 g of isophorone-diisocyanate were added and the mixture heated to 90° C. The reaction was effected with the addition of dibutylin dilaurate. When 50% of the isocyanate groups had reacted as indicated by titration, 10.0 g of tetra (hydroxypropyl)pentaerythritol triacrylate and 0.05 g of hydroquinone were added and the reaction continued until all isocyanate groups had disappeared. The solvent was removed in vacuo and a solid coloured material was obtained. Further tests showed the solid to be no longer soluble in common solvents indicating premature crosslinking during the reaction.

EXAMPLE 10

Synthesis of a photocrosslinkable monoazo dye—(Compound 38)

A monoazo dye of formula 4 (10.0 g) was reacted with 21.4 g of a monoisocyanate polyacrylate (compound 32) according to the method of Example 8. The product obtained was a viscous liquid and its chemical structure was confirmed by ¹H NMR and infrared spectroscopy.

EXAMPLE 11

Synthesis of a photocrosslinkable monoazo dye according to a prior art method

The photocrosslinkable monoazo dye of Example 10 was synthesised according to the method in GB 2,038,849. Thus, monoazo dye of formula 4 (10.0 g) was reacted with isophorone diisocyanate (6.1 g) and tetra(hydroxypropyl) pentaerythritol triacrylate (20.0 g) using the method of Example 9. The product obtained was in viscous liquid form with some insoluble particles.

EXAMPLE 12

Synthesis of a photocrosslinkable colour change dye—(Compound 39)

A pH-sensitive colour change dye of formula 2 (5.0 g) was reacted with 8.25 g of a monoisocyanate polyacrylate (compound 34) according to the method of Example 8 to obtain the product as a viscous liquid. The chemical structure of the product was confirmed by ¹H NMR and infrared spectroscopy.

EXAMPLE 13

Synthesis of a photocrosslinkable colour change dye—(Compound 40)

A pH-sensitive colour-change dye of formula 3 (5.0 g) was reacted with 10.1 g of a monoisocyanate polyacrylate (compound 34) according to the method of Example 8 to afford the product as a viscous liquid. The chemical structure of the product was confirmed by ¹H NMR and infrared spectroscopy.

EXAMPLE 14

Synthesis of a photocrosslinkable sensitiser—(Compound 41)

7.14 g of Compound 26 were dissolved in 50 mls of dry methyl ethyl ketone and to this solution were added 14.5 g of Compound 34 and 1 drop of dibutyltin dilaurate. The mixture was then heated to 50° C. and held at 50° C. for 6 hours. After infrared spectroscopy measurement confirmed that all the isocyanate groups had reacted, 5 mls of methanol were added and the reaction mixture further stirred for 2 hours. The solvent was removed in vacuo to afford the product as a viscous liquid. The chemical structure of the product was confirmed by ¹H NMR and IR spectroscopy.

EXAMPLE 15

Plate-testing of a photocrosslinkable binder resin—(Compound 35)

A solution in methyl ethyl ketone comprising:

2.00 parts of pentaerythritol tetraacrylate;

1.48 parts of Compound 35;

0.125 parts of 2(p-methoxyphenyl)4,6-bistrichloromethyl-5-triazine; and 0.08 parts of Victoria Pure Blue FGA was whirler coated onto a sheet of electrograined and anodised aluminium to give a coat weight of 1.2 g/m². The dried coating was overcoated with poly(vinyl alcohol) to prevent oxygen inhibition.

A comparative radiation sensitive plate was made using a solution in methyl ethyl ketone comprising:

2.55 parts of pentaerythritol tetraacrylate;

0.85 parts of Epikote 1004;

0.125 parts of 2(p-methoxyphenyl)4,6-bistrichloromethyl-5-triazine; and 0.08 parts of Victoria Pure Blue FGA The two radiation sensitive plates were exposed through a continuous tone Stouffer stepwedge to ultraviolet light (246 mJ/cm² from a Berkey-Ascor printing down frame) and then developed with a solution comprising butyrolactone, methoxy ethoxy ethanol and a surfactant. Both plates produced a stepwedge reading of solid 4, tail 8. When placed on a printing press the plate in accordance with the invention achieved 200,000 satisfactory impressions and the comparative plate achieved 125,000 satisfactory impressions.

EXAMPLES 16 TO 21

Plate-testing of the photocrosslinkable dyes of Examples 8–11 and comparisons

In these Examples, the photocrosslinkable dyes of Examples 8–11 and the two unmodified dyes were tested in the following photopolymerisable plate formulation:

2.55 parts of a polyfunctional photopolymerisable monomer, pentaerythritol tetraacrylate;

0.85 parts of a phthaloylated poly(vinyl butyral), with an acid value of 85.0;

0.125 parts of a photoinitiator, 2-(p-methoxyphenyl)-4,6-bistrichloromethyl-s-triazine; and 0.20 parts of the dye being tested In each case, a solution of the composition in methyl ethyl ketone was whirler coated onto a sheet of electrograined and anodised aluminium to give a coat weight of 1.0–1.2 g/m². The dried coating was overcoated with poly(vinyl alcohol) to prevent oxygen inhibition.

The resultant radiation sensitive plates were exposed through a continuous tone Stouffer stepwedge to ultra-violet light (246 mJ/cm² from a Berkey-Ascor printing down frame) and then developed with an aqueous solution containing sodium propanoate, sodium benzoate and a surfactant. The developed image of the resultant lithographic printing plates had the solid stepwedge steps indicated in Table I.

The colour leaching property of the image areas of the plates was determined by colour measurement comparisons and is expressed by the colour difference (ΔE) between the colour of the original plate and the colour after development.

TABLE I

| SENSITIVITY AND LEACHING RESISTANCE OF THE PLATES | | | |
|---|---|---|---|
| EXAMPLES | DYES | STOUFFER STEPWEDGE | COLOUR DIFFERENCE (ΔE) |
| 16 | Reactint Blue X3 | 5,8 | 22.44 |
| 17 | Photocrosslinkable Dye (Compound 37) | 5,8 | 8.56 |
| 18 | Prior Art dye of Example 9 | Not tested due to crosslinking | |
| 19 | Monazo Dye (Compound 4) | 4,7 | 12.9 |
| 20 | Compound 38 (Example 10) | 4,7 | 4.17 |
| 21 | Compound 38 (Example 11) | 4,7 | 5.75 |

A study of the above table reveals;

(i) The two unmodified dyes, Reactint Blue X3 of Example 16 and the monazo dye of Example 19 both showed severe colour-leaching as reflected by the high colour difference values. The colour difference values are significantly reduced when the dyes are made photocrosslinkable as in Examples 17, 20 and 21.

(ii) The prior art method suffers from two problems. In terms of synthesis method, it showed inconsistency, especially when modification of dyes of relatively high molecular weight or dyes of the polyhydroxy type was attempted. Premature crosslinking took place. Also lack of leaching resistance was still evident despite the attempt to confer photocrosslinkability. This was due to the existence in the final product of the non-photocrosslinkable form of the dye as is clearly demonstrated by comparing the colour differences in Examples 20 and 21.

EXAMPLE 22

Plate-testing of a photocrosslinkable colour change dye

The photocrosslinkable colour change dye synthesised in Example 13 (Compound 40) was tested according to the formulation used in Examples 16 to 21

As a comparison, the colour change dye of formula 3 was tested using the same method as above.

The colour leaching property of the image areas of the plates was determined by colour measurement and was expressed by the colour difference between the original plate colour and that after development (ΔE). The results are shown in Table II.

TABLE II

| COLOUR LEACHING PROPERTY OF THE PHOTOCROSSLINKABLE DYE | | |
|---|---|---|
| DYES | STOUFFER'S STEPWEDGE | COLOUR DIFFERENCE (ΔE) |
| Photocrosslinkable dye (Compound 40) | 4,7 | 2.75 |
| Unmodified dye (Compound 3) | 4,7 | 15.91 |

EXAMPLE 23

Plate-testing of a photocrosslinkable sensitiser (Compound 41)

A solution in ethyl methyl ketone of a photopolymerisable composition comprising:

3 parts by weight of the dimethacrylate ester of the diglycidyl ether of bisphenol A;

1 part by weight of a vinyl acetate/crotonic acid copolymer;

0.43 parts by weight of tristrichloromethyl-s-triazine; and 0.45 parts by weight of Compound 41 was whirler coated onto a sheet of electrograined and anodised aluminium and dried to form a radiation sensitive plate with a coating weight of 1.2 g/m². The dried coating was overcoated with poly(vinyl alcohol) to prevent oxygen inhibition of the photopolymerisation reaction.

The radiation sensitive plate was exposed through a continuous tone Stouffer stepwedge to ultraviolet light (20 mJ/cm² from a Berkey-Ascor printing down frame) and then developed with an aqueous solution containing sodium propanoate, sodium benzoate and a surfactant. The developed image had a step wedge of solid 4, tail 8.

A comparative plate was made using the above composition except that 0.15 parts by weight of ethyl Michler's ketone was used in place of Compound 41. The radiation sensitive plate was processed and developed using the same method as above to give a step wedge of solid 4, tail 8.

After storage under accelerated ageing conditions (30° C., 95% relative humidity for 3 weeks), analysis of the radiation sensitive plate of the invention showed negligible migration of Compound 41, while a loss of 33% of ethyl Michler's ketone was found in the comparative plate indicating that substantial migration had taken place.

Exposure and development of the aged plates gave the plate of the invention a stepwedge of solid 4, tail 8 and the comparative plate, a stepwedge of solid 2, tail 6.

EXAMPLE 24

Plate-testing of a photocrosslinkable dye— (Compound 37) and comparative example A solution in ethyl methyl ketone of a photopolymerisable composition comprising:

1 part by weight of pentaerythritol tetraacrylate;

2.5 parts by weight of phthaloylated poly(vinyl butyral), with an acid value of 85.0;

0.1 parts by weight of 2-methoxyphenyl-4,6-bistrichloromethyl-s-triazine;

0.2 parts by weight of a diazodiphenylamine formaldehyde condensate $PF_6^-$; and 0.2 parts by weight of Compound 37 was whirler coated onto a sheet of electrograined and anodised aluminium to give a coat weight of 1.2 $g/m^2$. The resultant radiation sensitive plate was exposed through a continuous tone Stouffer stepwedge to ultraviolet light (246 $mJ/cm^2$ from a Berkey-Ascor printing down frame) and then developed with an aqueous solution containing sodium propanoate, sodium benzoate and a surfactant. The developed image had a stepwedge of solid 4, tail 8. The colour difference (CIELAB) between the unexposed plate and the image area of the plate after development was 2.4.

A comparative example was made using the above formulation, but 0.1 g of the commercial Reactint Blue X3 was used in place of Compound 37. The resultant plate was processed in the same manner as above. The developed image had a stepwedge of solid 4, tail 10. The colour difference between the unexposed plate and the image area of the developed plate was 22.

The colour leaching property of the plate of the invention was therefore superior.

(1)

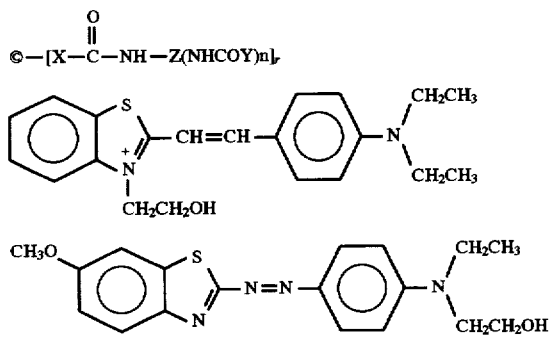

(2)

(3)

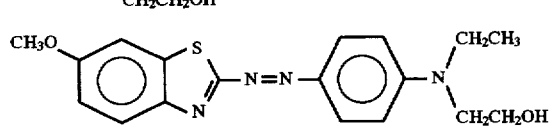

(4)

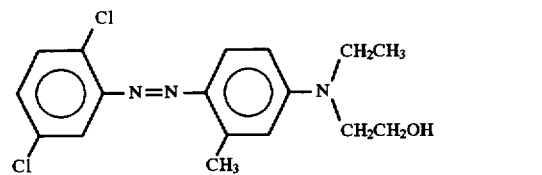

(5)

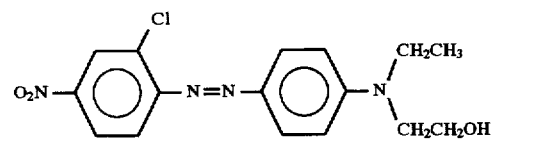

(6)

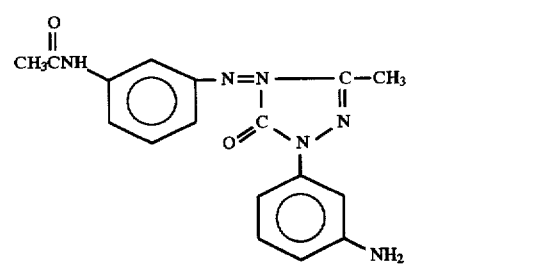

(7)

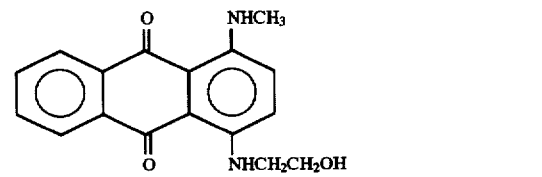

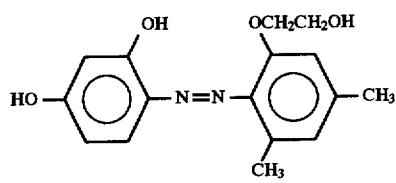
(8)
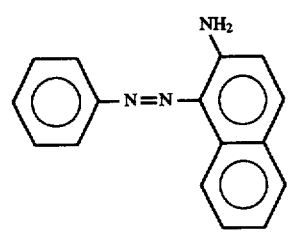
(9)
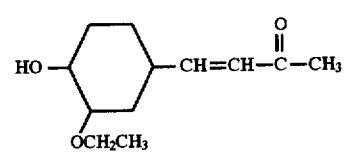
(10)
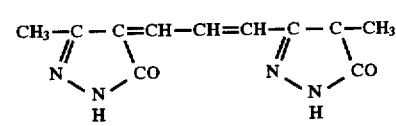
(11)
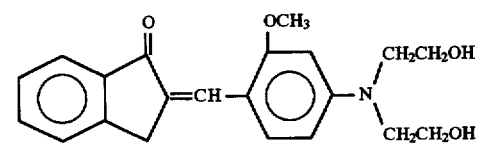
(12)
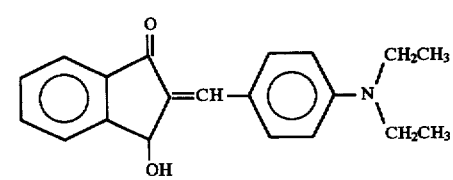
(13)
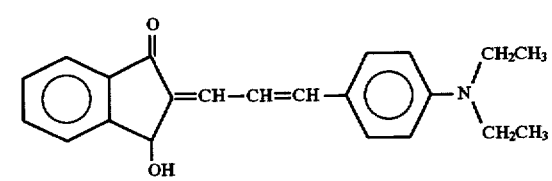
(14)
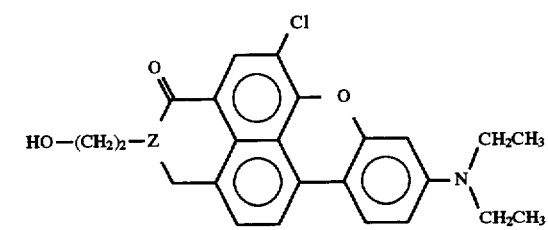
(15)

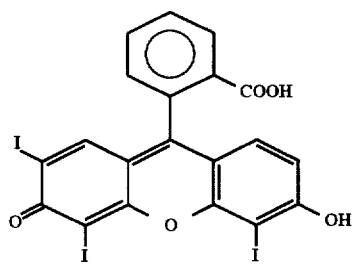
(16)
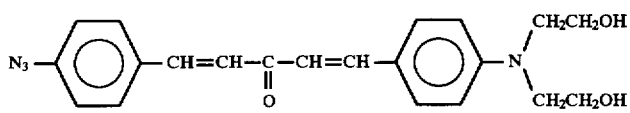
(17)
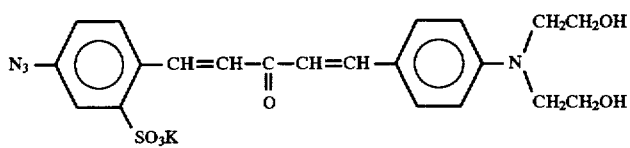
(18)
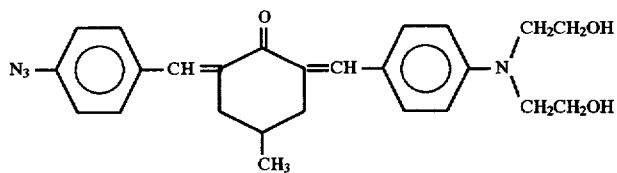
(19)
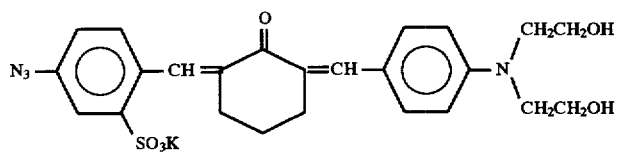
(20)
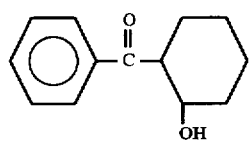
(21)
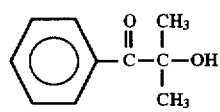
(22)
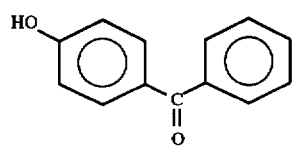
(23)
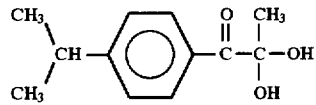
(24)
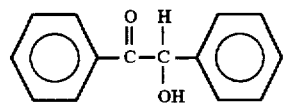
(25)

-continued
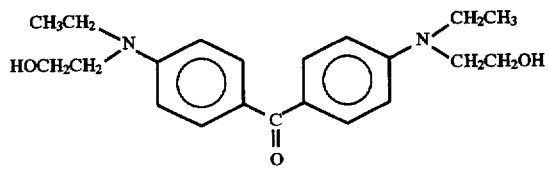
(26)
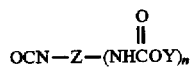
(27)
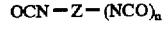
(28)
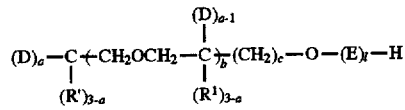
(29)
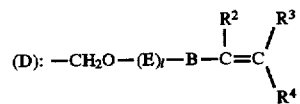
(30)
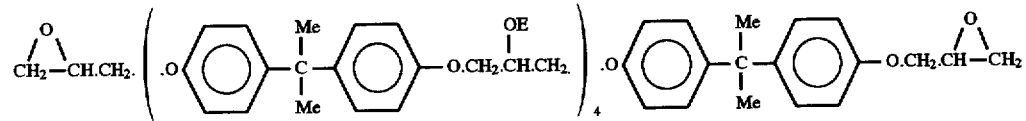
(35)
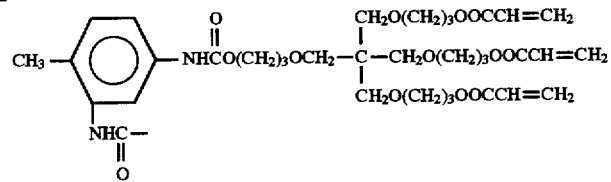
(31)
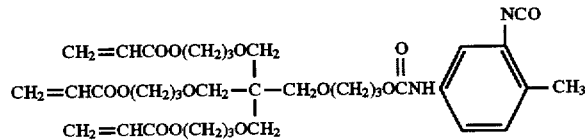
(32)
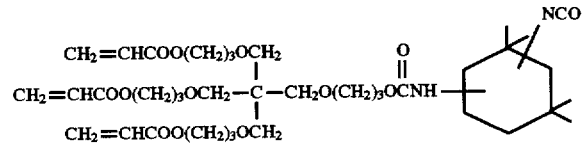
(33)
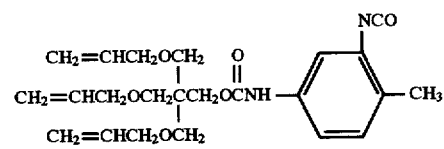
(34)
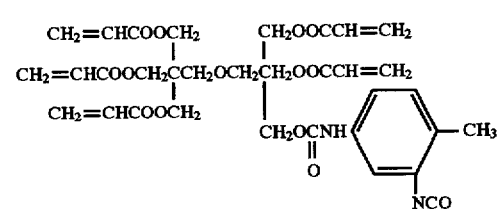

-continued
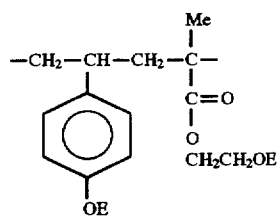
(36)
E = 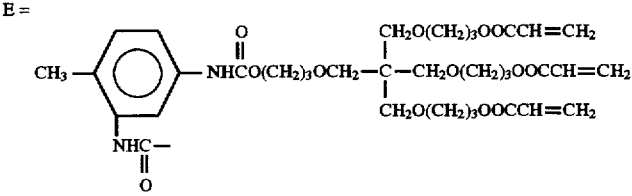
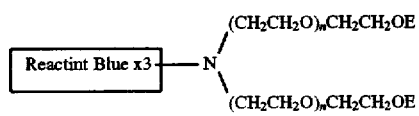
(37)
E = 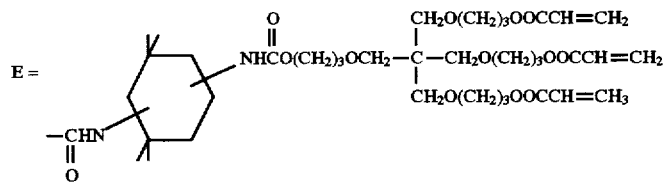
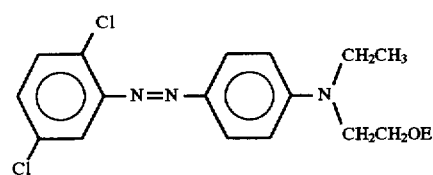
(38)
E as in Formula 37.
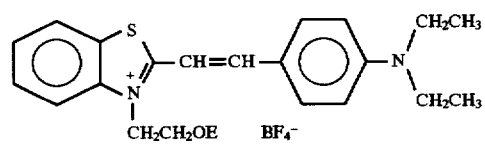
(39)
E = 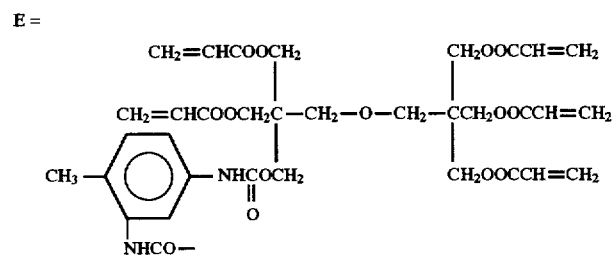
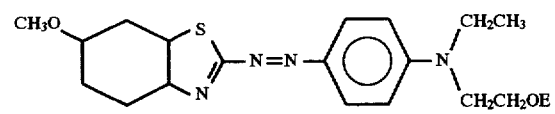
(40)
E as in Formula 39

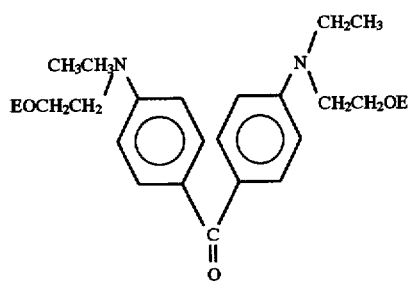
E as Formula 39
(40)
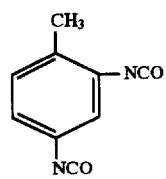
(42)
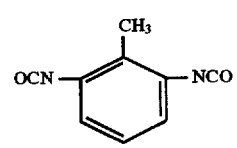
(43)
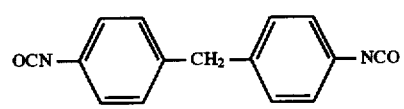
(44)
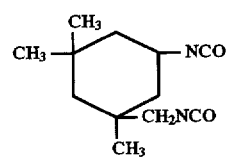
(45)
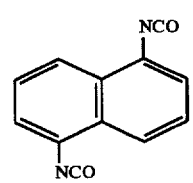
(46)
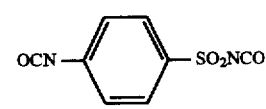
(47)
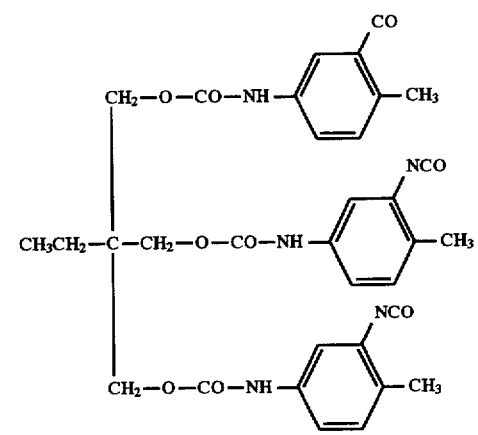
(48)
(49)

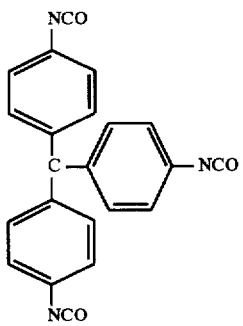 (50)

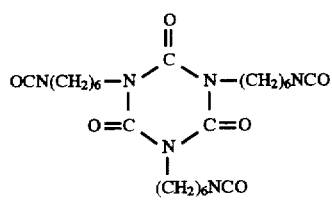 (51)

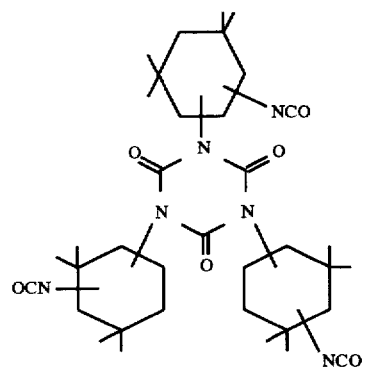 (52)

We claim:

1. A process for producing a polyunsaturated compound which comprises
   (a) forming a mono isocyanate compound having the formula

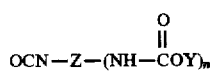

by reacting a compound YOH with a polyisocyanate OCN—Z—(NCO)$_n$ where n is 1 or 2; Z represents the residue of a polyisocyanate OCN—Z—(NCO)$_n$, and Y is the residue of a monohydroxyl compound of the formula YOH where Y contains at least two ethylenically unsaturated double bonds in a reaction medium in which said compound YOH and said polyisocyanate are miscible and said mono isocyanate compound is immiscible;
   (b) recovering said mono isocyanate compound from said reaction medium, and reacting a compound of the formula ⊙-(XH)$_r$ with said mono isocyanate compound wherein ⊙ represents the residue of an active hydrogen containing compound of the formula ⊙-(XH)$_r$ where XH is a hydroxyl group, a mercapto group or a primary or secondary amino group; and r is an integer ranging from 1 to 10 for a simple molecule and from 1 to 10,000 for a polymeric macromolecule.

2. The process of claim 1 wherein said compound ⊙-(XH)$_r$ is an organic colorant or a chromophore functioning as a shading dye or colour-change dye, an anti-halation reagent, a photosensitizer, an organic azide photoactive material, a photoinitiator, a polymeric binder resin, or an isocyanate blocking agent.

3. The process of claim 2 wherein said polymeric binder resin is a poly(vinyl acetal), a styrene-allyl alcohol copolymer, an acrylic co- or terpolymer containing hydroxy alkyl methacrylate, a novolak resin or a poly(vinyl phenol).

4. The process of claim 1 wherein said ethylenically unsaturated compound YOH has the formula:

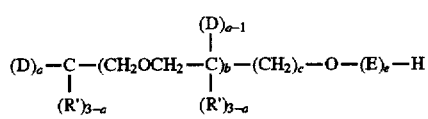

where:

(i) a is 2 or 3; b, c, and e are 0 or 1; R' is hydrogen or alkyl;
(ii) D has the structure:

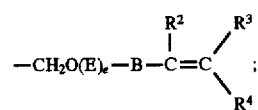

(iii) E has the structure:

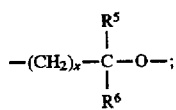

(iv) B is a single bond, —CH$_2$—, or

and (v) x is 1 to 3, and R$^2$ through R$^6$ are independently H or CH$_3$.

5. A polyunsaturated compound having the general formula:

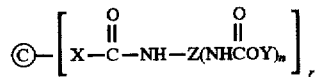

where Ⓒ represents the residue of an active hydrogen containing compound of the formula Ⓒ-(XH)$_r$ where XH is a hydroxyl group, a mercapto group or a primary or secondary amino group; and r is an integer ranging from 1 to 10 for a simple molecule and from 1 to 10,000 for a polymeric macromolecule, Z represents the residue of a polyisocyanate OCN—Z—(NCO)$_n$, where n is 1 or 2;

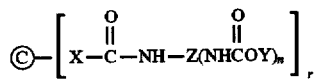

is provided by a pure polyethylenically unsaturated monoisocyanate of the formula

and Y is the residue of a monohydroxy compound of formula YOH where Y contains at least two ethylenically unsaturated double bonds, with the proviso that said active hydrogen containing compound is an organic colorant or a chromophore functioning as a shading dye or colour-change dye, an anti-halation reagent, a photosensitizer, an organic azide photoactive material, a photoinitiator, a polymeric binder resin, or an isocyanate blocking agent.

6. The compound of claim 5 wherein said compound Ⓒ-(XH)$_r$ is an organic anti-halation reagent or a photosensitizer which is a monazo, methine or polycyclic derivative.

7. The compound of claim 5 wherein said polymeric binder resin is a poly(vinyl acetal), a styrene-allyl alcohol copolymer, an acrylic co- or terpolymer containing hydroxy alkyl methacrylate, a novolak resin or a poly(vinyl phenol).

8. The compound of claim 5 wherein said isocyanate blocking agent is an oxime, phenol or caprolactam.

* * * * *